United States Patent
Kang et al.

(10) Patent No.: US 7,241,901 B2
(45) Date of Patent: Jul. 10, 2007

(54) PROCESS FOR PREPARING THIAZOLE DERIVATIVE AND THE INTERMEDIATE COMPOUNDS FOR PREPARING THE SAME

(76) Inventors: Heonjoong Kang, 412-305 Saetbyeolmaeul Bundang-dong 39 Seongnam-si, Gyeonggi-do (KR); Jungyeob Ham, 123-404, Gwanak dream town, Bongcheon-dong, Gwanak-gu, Seoul (KR) 151-770

( * ) Notice: Subject to any disclaimer, the term of this patent is extended or adjusted under 35 U.S.C. 154(b) by 64 days.

(21) Appl. No.: 10/513,408

(22) PCT Filed: May 1, 2003

(86) PCT No.: PCT/KR03/00877

§ 371 (c)(1),
(2), (4) Date: Nov. 4, 2004

(87) PCT Pub. No.: WO03/106442

PCT Pub. Date: Dec. 24, 2003

(65) Prior Publication Data
US 2005/0176785 A1    Aug. 11, 2005

(30) Foreign Application Priority Data
May 4, 2002    (KR)    ............... 10-2002-0024595

(51) Int. Cl.
*C07D 277/26*    (2006.01)
(52) U.S. Cl. .................................... 548/204
(58) Field of Classification Search .............. None
See application file for complete search history.

(56) References Cited

U.S. PATENT DOCUMENTS

2005/0159598 A1 * 7/2005 Ingold et al. ............... 540/603

FOREIGN PATENT DOCUMENTS

| WO | WO 99/46232 | 9/1999 |
| WO | WO 01/00603 | 1/2001 |
| WO | WO 02/50047 | 6/2002 |
| WO | WO 02/070011 | * 9/2002 |

OTHER PUBLICATIONS

Willson et al., STN International, HCAPLUS Database, Columbus, OH, Accession No. 2002:695816 (2006).*
Marcos et al. "Novel selective small molecule agonists for peroxisome proliferator-activated receptor delta (PPAR delta)-synthesis and biological activity" Bioorg. Med. Chem. Lett. 13:1517-1521 (2003).
International Search Report for PCT/KR2003/000877, dated Jul. 15, 2003.
International Preliminary Examination Report for PCT/KR2003/000877, dated Aug. 18, 2004.

* cited by examiner

*Primary Examiner*—Joseph K. McKane
*Assistant Examiner*—Andrew B. Freistein
(74) *Attorney, Agent, or Firm*—Nixon & Vanderhye P.C.

(57) ABSTRACT

The present invention provides a process for preparing thiazole derivatives of formula (XI), that activate the delta subtype of the human Peroxisome Proliferator Activated Receptor (hPPARδ), and also provides processes for compounds of formula (VI), (VII), (VIII) and (IX), intermediate compounds for preparation of the above compounds of formula (XI).

9 Claims, No Drawings

PROCESS FOR PREPARING THIAZOLE DERIVATIVE AND THE INTERMEDIATE COMPOUNDS FOR PREPARING THE SAME

TECHNICAL FIELD

The present invention relates to a process for preparing thiazole derivative of formula (XI), that activates the delta subtype of the human Proxisome Proliferator Activated Receptor (hPPARδ), and also relates to the compounds of formula (VI), (VII), (VIII) and (IX), intermediate compounds for preparation of the above compound of formula (XI).

BACKGROUND ART

Especially, 2-{2-methyl-4-[({4-metyl-2-[4-(trifluoromethyl)phenyl]-1,3-thiazole-5-yl}methyl)sulfonyl]phenoxy}acetic acid (hereinafter, called to "GW501516") among thiazole derivatives of formula (XI) showed an excellent effect to treatment of obesity in animal models (*Cell* 2003, 113, 159), and proved effectiveness in cardio-vascular disease by increasing high density lipoprotein (HDL) and decreasing low density lipoprotein (LDL) effectively in the animal experiment (*Proc. Natl. Acad. USA* 2001, 98, 5306) and in clinical trial. And the process for preparation of the said substance has been disclosed in PCT publication WO 01/00603A1 and *Bioorg. Med Chem. Lett.* 2003, 13, 1517, in which GW501516 (13) was prepared, as shown in the following scheme(1). Methyl (4-mercapto-3-methylphenoxy)acetate (7), synthesized from the starting material, 4'-hydroxy-3'-methylacetophenone (1), via 6 steps, was coupled to 5-chloromethyl-4-methyl-2-(4-trifluoromethyl-phenyl)thiazole (11), which was prepared from 4-(trifluoromethyl)thiobenzamide (8) via 3 steps, in the presence of excessive cesium carbonate to obtain the methyl ester (12) of GW501516, and then treating the ester with 1 N lithium hydroxide to give GW501516.

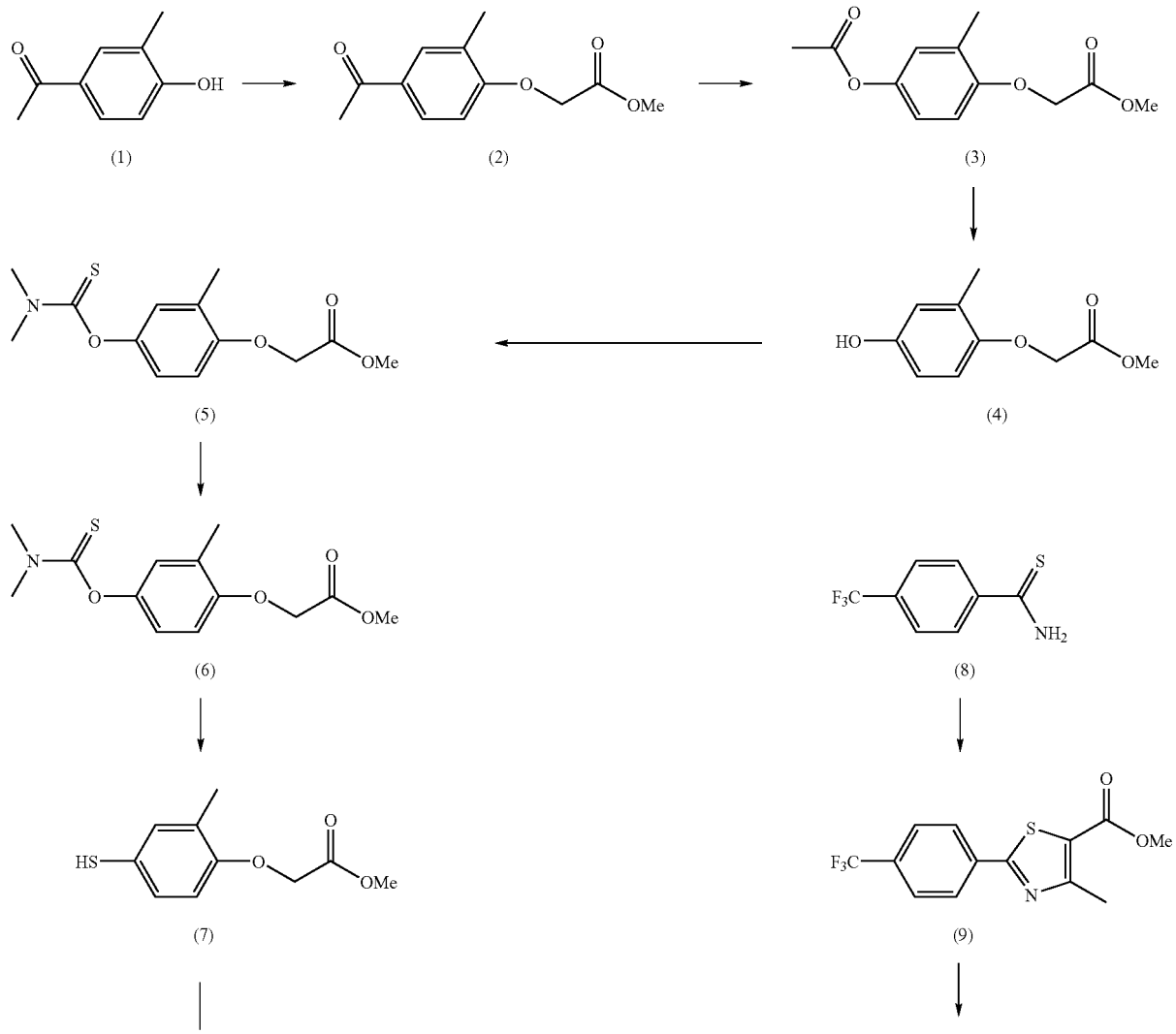

Reaction scheme (1)

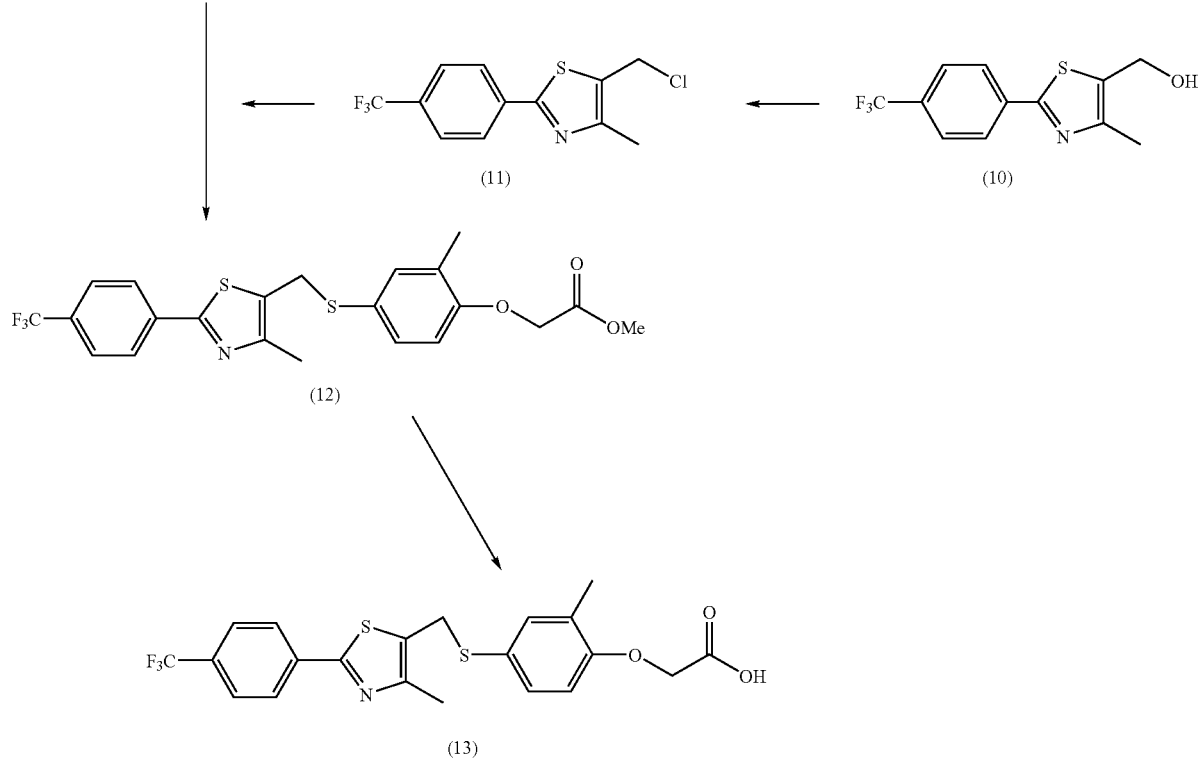

As an alternative synthesis method of GW501516, it is disclosed as illustrated in the following scheme (2), that the compound (13) of GW501516 can be prepared by introducing ethyl acetate group to o-cresol (14), reacting the resulted coruppund (15) with sulfonyl chloride, reducing the resulted compound (16) with tin (Sn) under acidic condition to form ethyl (4-mercapto-2-methyl phenoxy)acetate (17), reacting it with 5-chloromethyl-4-methyl-2-(4-trifluoromethyl phenyl)thiazole (11) together with an excessive cesium carbonate to obtain the ethyl ester intermediate (18) of GW501516, and deprotecting the ester group of the intermediate compound with 1 N lithium hydroxide.

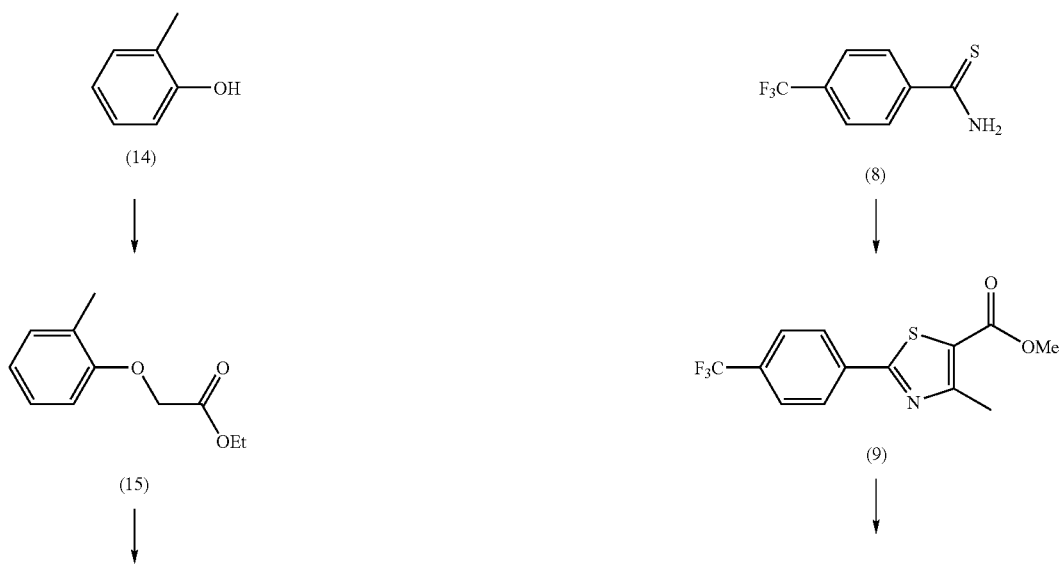

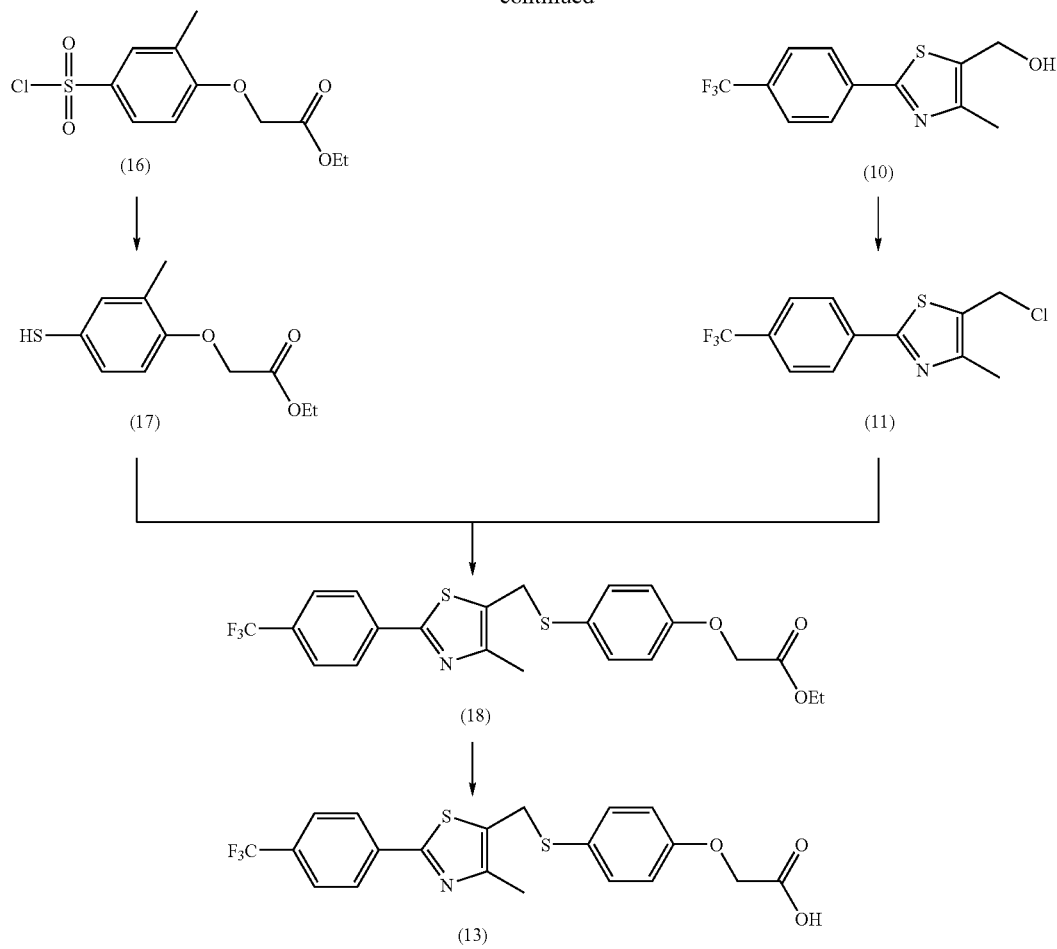

Although the above compound (13) has known to be an excellent efficacy in the treatment of obesity in animal models and in the treatment of disease states associated with cholesterol metabolism in clinical trials, the manufacturing method thereof was not satisfactory, thereby being not cost-effective. That is to say, 1) The manufacturing method of reaction scheme (1) consists of 12 steps, and the total yield thereof is as low as 2%. So, it is not proper to be applied to the industry, due to its extreme low production yield.
2) The manufacturing process according to the reaction scheme (1) includes three refluxing steps at elevated temperature for 16 hours, which takes long time to obtain the final product.
3) Tin (Sn) powder used in reaction scheme (2) is very unstable to the moisture, and moreover, it is a combustible metal, thereby being very dangerous to adopt it in industrial scale.
4) An excessive tin (Sn) powder used in the reaction scheme (2) may lead to pollution of the environment.
5) A separated another step for reacting compound (11) with compound (7) or compound (17) in the reaction scheme (1) or (2) is required, and also an excess amount of cesium carbonate, which is not common inorganic base, is used, and also the reaction time is comparatively long.
6) The hydrolysis steps of methyl or ethyl ester using 1 N lithium hydroxide in reaction scheme (1) or (2) requires a long reaction time, about 16 hours, of which yield is as low as 60%.
7) Methyl or ethyl (4-mercapto-2-methylphenoxy)acetate (7) or (17) obtained as an intermediate compound in the reaction scheme (1) or (2) is unstable, so the respective compound can be easily changed to disulfides, which results in lowering the total reaction yield.

Under the circumstance, the novel process for preparing the above compound with easiness and low cost has been demanded in the art.

DISCLOSURE OF THE INVENTION

In view of the above situation, the inventors of the present invention have conducted extensive studies on the novel processes for preparing compounds of the following formula (XI). As a result, the inventors have found that the said compounds can be easily prepared as shown in the following reaction scheme. That is to say, 4-halogenated phenols of formula (V) are converted into compounds of formula (VI) which are stable to the base, the halogen group of compound (VI) is substituted with metal such as lithium or magnesium, and then they are converted into the metal thiolate intermediate compounds of formula (VII), using sulfur. The compounds (VII) are reacted with compounds of formula (IV) without separation and purification step, which are prepared from compounds of formula (I) via several steps, to obtain thioether compounds of formula (VIII) easily. It is subjected to deprotecting the phenol residue to get compounds of formula (IX), which are reacted with alkyl halogenated acetate to give compounds of formula (X), and then they are hydrolyzed to have compounds of formula (XI).

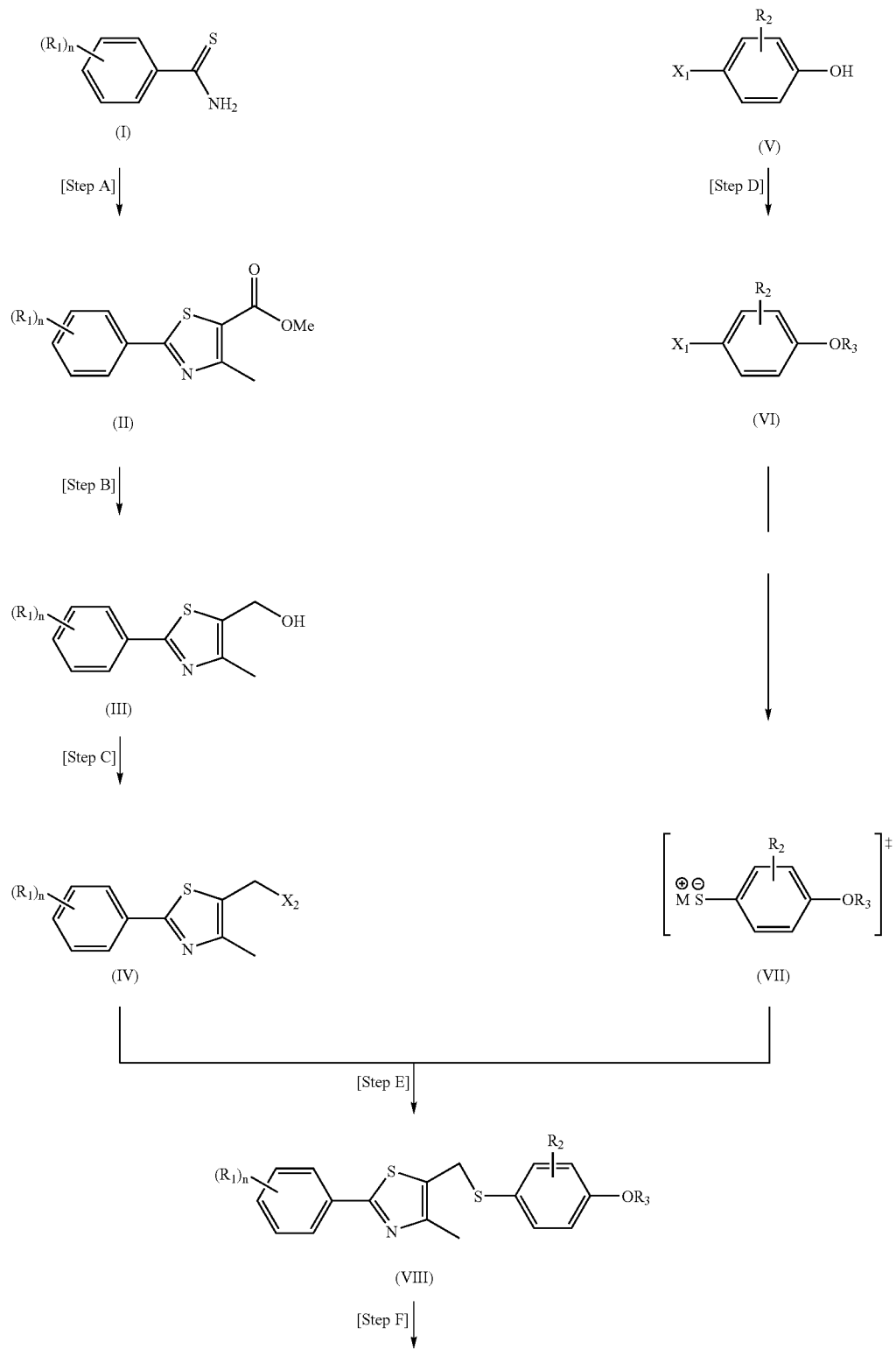

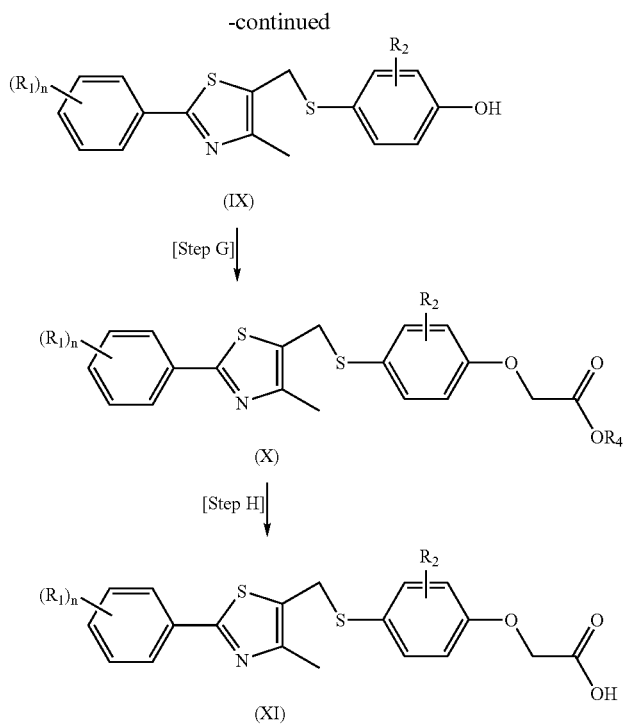

(IX)

[Step G]

(X)

[Step H]

(XI)

wherein, $R_1$ represents hydrogen atom, $CF_3$, or halogen atom, n is an integer of 0 to 5, $R_2$ represents a hydrogen atom, fluorine atom, chlorine atom, —($C_1$-$C_4$) alkyl, —O($C_1$-$C_4$) alkyl, —S($C_1$-$C_4$) alkyl, or —N($C_1$-$C_4$alkyl)$_2$ group, $R_3$ represents a protecting group having a tetrahydropyranyl. —($C_1$-$C_4$) alkyl, allyl, or silyl group such as alkylsilyl, alkylarylsilyl, $R_4$ represents a —($C_1$-$C_4$) alkyl group, $X_1$ represents a halogen atom, $X_2$ represents a halogen atom, or leaving group easily displaced by nucleophiles, and M represents a lithium ion or magnesium halide (Cl, Br, or I).

An object of the present invention is to provide a process for preparing compounds of formula (XI) in high yield in a short period, via unstable intermediate compounds without separation step in the reaction.

The present invention also provides a process for preparing compounds of formula (II), which comprises by reacting compounds of formula (I) with alkyl 2-chloroacetoacetate.

The present invention further provides a process for preparing compounds of formula (III), which comprises by reducing the ester group of compounds of formula (II).

The present invention further provides a process for preparing compounds of formula (IV), which comprises by introducing a leaving group to compounds of formula (III).

The present invention further provides a process for preparing compounds of formula (VI), which comprises by reacting compounds of formula (V) with a phenol protecting group.

The present invention further provides a process for preparing compounds of formula (VIII), which comprises by reacting compounds of formula (VI) with metallic or organometallic reagents and sulfur to form compounds of formula (VII), and reacting them with compounds of formula (IV) without a specific organic or inorganic base.

The present invention further provides a process for preparing compounds of formula (IX), which comprises by eliminating the protecting group of phenol of compounds of formula (VIII).

The present invention further provides a process for preparing compounds of formula (X), which comprises by reacting compounds of formula (IX) with alkyl haloacetate in the presence of organic or inorganic base.

The present invention further provides a process for preparing compounds of formula (XI), which comprises by subjecting the ester compounds of formula (X) to hydrolyze.

The present invention further provides processes for the novel compounds of formula (VI), (VII), (VIII), and (IX), each of which useful as intermediate compounds for preparation of the final products of the present invention.

BEST MODE FOR CARRYING OUT THE INVENTION

In a process for preparation of compounds of formula (XI) according to the present invention, $R_1$ represents hydrogen atom, $CF_3$, or halogen atom, and the number (n) of the substituent is 0 to 5 of the same or different one.

$R_2$ stands for hydrogen atom, fluorine atom, chlorine atom, —O-alkyl, —S-alkyl, or —N-(alkyl)$_2$ (alkyl group having 1 to 4 carbon atoms). The position of each substituent is ortho- or meta- to the phenol group, and the number of substituent is 1 or 2.

$R_3$ is a protecting group, and includes a tetrahydropyranyl, alkyl or allyl group having 1 to 4 carbon atoms, or silyl group such as trimethylsilyl, tert-butyldimethylsilyl, tert-butyldiphenylsilyl. Preferred examples of the protecting groups among them include tert-butyl, tetrahydropyranyl and silylated groups.

$R_4$ is a protecting group, and examples thereof include alkyl having 1 to 4 carbon atoms such as methyl, ethyl, propyl, isopropyl, n-butyl, and tert-butyl group. Of these, methyl, ethyl, and propyl are preferred.

Example of the halogen atom represented by $X_1$ includes a fluorine atom, chlorine atom, bromine atom or iodine atom.

$X_2$ represents a leaving group, which can be easily displaced by metal thiolate in nucleophilic substitution reaction.

Examples thereof include a halogen atom, methanesulfonate (MsO—), and p-tolunesulfonate (TsO—). Here, the halogen atom means a fluorine atom, chlorine atom, bromine atom or iodine atom.

M represents a lithium ion or magnesium halide (Cl, Br, or I).

The compounds of the formula (I) and (V) are commercially available or can be synthesized easily by using known methods in the art.

The process of the present invention will be described as set below.

[Step A] Preparation of Compounds of Formula (II):

Compounds of formula (II) can be prepared by reacting compounds of formula (I) with ethyl or methyl 2-chloroacetoacetate in a solvent.

Suitable solvents usable in this reaction include alcohols such as methanol, ethanol, propanol, and butanol; and ethers such as diethyl ether, tetrahydrofuran, and 1,4-dioxane. Of these, ethanol or tetrahydrofuran is preferred as a solvent.

The reaction time and temperature depend on the solvent to be used. However, it is preferred to conduct the reaction at 25 to 150° C. for 6 hours to 1 day, more preferably 60 to 120° C. within 16 hours.

[Step B] Preparation of Compounds of Formula (III):

Compounds of formula (III) can be prepared by reducing the ester moiety of compounds of formula (II) in an anhydrous solvent.

As reducing agents, aluminum hydrides such as lithium aluminum hydride, and diisobutylaluminum hydride, and boron hydrides such as sodium borohydride and lithium borohydride can be given. Among them, lithium aluminum hydride and diisobutylaluminum hydride are preferred.

As anhydrous solvents usable in this reaction, diethyl ether, tetrahydrofuran, and dichloromethane can be given, with preferably, dichloromethane.

The reaction time and temperature depend on the solvent to be used. However, it is preferred to conduct the reaction at −100 to 60° C. for 30 minutes to 6 hours, more preferably −78 to 25° C. within 2 hours.

[Step C] Preparation of Compounds of Formula (IV):

Compounds of formula (IV) can be prepared by subjecting halogenation reaction on compounds of formula (III), or reacting compounds of formula (III) with methanesulfonyl chloride or p-toluene sulfonyl chloride in a solvent.

Suitable solvents usable in this include N,N-dimethylformamide, diethyl ether, tetrahydrofuran, tetrachloromethane, chloroform, dichloromethane, and pyridine. Of these, dichloromethane for halogenation reaction, and pyridine for methanesulfonate or p-toluenesulfonate reaction respectively are preferred.

Suitable reagents for halogenation reaction to the alcohol moiety include triphenylphosphine (TPP) with N-chlorosuccinimide (NCS), triphenylphosphine with chlorine gas, triphenylphosphine with tetrachloromethane($CCl_4$), phosphorus pentachloride ($PCl_5$), thionylchloride ($SOCl_2$), and methanesulfonyl chloride ($MeSO_2Cl$) for introduction of chlorine atom; triphenylphosphine with N-bromosuccinimide (NBS), triphenylphosphine with bromine gas, triphenylphosphine with tetrabromomethane ($CBr_4$), phosphorus pentabromide ($PBr_5$), and thionyl bromide ($SOBr_2$) for introduction of bromine atom; triphenylphosphine with N-iodosuccine imide, triphenylphosphine with solid iodine, and triphenylphosphine with tetraiodomethane ($CI_4$) for introduction of iodine atom. Alternatively, introduction of iodine atom can be carried out by substituting chloro- or bromocompounds of formula (IV) with sodium iodide(NaI) in acetone, so-called halogen-iodine substitution method. Of these, the preferred leaving group is chlorine or bromine atom, and the preferred reagent for this reaction is triphenylphosphine with N-chlorosuccinimide or N-bromosuccinimide.

The reaction time and temperature depend on the solvent to be used. However, it is preferred to conduct this reaction at −10 to 40° C. for 30 minutes to 1 day, more preferably 10 to 25° C. within 2 hours.

[Step D] Preparation of Compounds of Formula (VI):

Compounds of formula (VI) can be prepared by reacting compounds of formula (V) with conventional compounds for protecting phenol group in the presence of a base in a solvent.

Suitable solvents usable in this reaction include N,N-dimethylformamide, N,N-dimethylacetamide, dimethyl sulfoxide, acetonitrile, acetone, ethyl acetate, tetrachloromethane, chloroform, and dichloromethane as aprotic polar solvents; tetrahydrofuran, 1,4-dioxane, dimethoxy ethane, and diethylene glycol dimethyl ether as ethers; and benzene, toluene, and xylene as aromatic hydrocarbons. Of these, an aprotic polar solvent is preferred, with N,N-dimethylformamide, chloroform, or dichloromethane being particularly preferred.

Suitable base usable for reacting silyl protecting group with phenol include amines such as pyridine, triethylamine, imidazole, and N,N-dimethylaminopyridine.

Suitable bases usable for reacting aryl ether protecting group with phenol include sodium hydroxide, potassium hydroxide, sodium carbonate, and potassium carbonate. As the preferred bases among the above, imidazole and potassium carbonate can be given.

Tetrahydropyranyl (THP) protection on the phenol group can be achieved by reacting 3,4-dihydro-2H-pyran with alkyl or aryl triphenylphosphonium bromide.

The reaction time and temperature depend on the solvent to be used. However, it is preferred to conduct this reaction at −10 to 80° C. for 1 hour to 1 day, more preferably 0 to 25° C. within 4 hours.

[Step E] Preparation of Compounds of Formula (VIII):

Compounds of formula (VIII) can be prepared by reacting intermediate compounds of formula (VII), without separation, with compounds of formula (IV) in an anhydrous solvent.

Suitable anhydrous solvents usable in this reaction include diethyl ether, tetrahydrofuran, hexane, and heptane. These solvents may be used either singly or in combination of two. Diethyl ether, tetrahydrofuran, and a mixed solvent of diethyl ether with tetrahydrofuran are particularly preferred.

As suitable metallic reagents used for halogen-metal substitution, lithium metal and magnesium metal can be given, and as organometallic reagents, n-butyllithium, sec-butyllithium, and tert-butyllithium can be used. Of these, organometallic reagents are preferred, with n-butyllithium and tert-butyllithium being particularly preferred.

The reaction time and temperature depend on the solvent to be used. However, it is preferred to conduct this reaction at −100 to 25° C. for 30 minutes to 1 day, more preferably in the step of sulfur introduction at −78° C., later raising the reaction temperature up to 25° C. for 1 hour after introduction of compounds of formula (IV) into the reaction mixture.

[Step F] Preparation of Compounds of Formula (IX):

Compounds of formula (IX) can be prepared by eliminating the phenol-protecting group of compounds of formula (VIII) in a solvent.

Suitable solvents usable in this reaction include N,N-dimethylformamide, N,N-dimethylacetamide, dimethyl sulfoxide, acetonitrile, acetone, ethyl acetate, tetrachloromethane, chloroform, and dichloromethane as polar solvents; tetrahydrofuran, 1,4-dioxane, dimethoxy ethane, and diethylene glycol dimethyl ether as ethers; and benzene, toluene, and xylene as aromatic hydrocarbons. Of these, tetrahydrofuran is particularly preferred.

Suitable reagents for elimination of the protecting groups of methyl, ethyl, tert-butyl, benzyl, allyl on the phenol group include a Lewis acid such as trimethylsilyliodide, ethane thioalcohol, lithium iodide, aluminum bromide, aluminum chloride, boron triiodide, and trifluoroacetic acid; suitable reagents for elimination of silylated protecting groups such as trimethylsilyl, tert-butyldiphenylsilyl, triisopropylsilyl, tert-butyldimethylsilyl include tetrabutylammonium fluoride, hydrochloric acid, hydrobromic acid, hydroiodic acid, and potassium fluoride. Of these, tetrabutylammonium fluoride is preferred for eliminating the silyl-protecting group on the phenol.

The reaction time and temperature depend on the solvent to be used. However, it is preferred to conduct this reaction at 0 to 120° C. for 30 minutes to 1 day, more preferably 10 to 25° C. within 2 hours.

[Step G] Preparation of Compounds of Formula (X):

Compounds of formula (X) can be prepared by reacting compounds of formula (IX) with alkyl halogen acetates in the presence of a base in a solvent.

The alkyl halogen acetates are commercially available or can be synthesized by known methods in the art. The alkyl group and halogen therein include methyl, ethyl, tert-butyl and a chlorine atom, bromine atom, and iodine atom, respectively. The most preferred one among the alkyl halogen acetates is methyl (or ethyl) chloro (or bromo)acetate.

Suitable solvents usable in this reaction include N,N-dimethylformamide, N,N-dimethylacetamide, dimethyl sulfoxide, acetonitrile, and acetone, with acetone being particularly preferred.

There is no specific limitation to bases used regardless of basicity, inasmuch as the base does not affect the reaction. Suitable bases include sodium hydride, lithium hydride, potassium hydride, sodium hydroxide, potassium hydroxide, lithium carbonate, sodium carbonate, sodium bicarbonate, potassium carbonate, and potassium bicarbonate. Of these, alkali metal hydride or alkali metal carbonate is preferred, with potassium carbonate being particularly preferred.

The reaction time and temperature depend on the solvent to be used. However, it is preferred to conduct this reaction at −10 to 120° C. for 30 minutes to1 day, more preferably 0 to 25° C. within 4 hours.

[Step H] Preparation of Compounds of Formula (XI):

Compounds of formula (XI) can be prepared by subjecting hydrolysis of the carboxylic ester of compounds of formula (X) in the presence of a water-soluble inorganic base and alcohol solvent.

Suitable solvents usable in this reaction include methanol, ethanol, and water miscible organic solvents.

As a base usable in this reaction, about 0.1 to 6 N aqueous solution of alkali metal hydroxide, such as lithium hydroxide, sodium hydroxide, or potassium hydroxide, is used. Of these, 1 to 3 N sodium hydroxide is preferred.

The reaction time and temperature depend on the solvent to be used. However, it is preferred to conduct this reaction at −10 to 80° C. for 10 minutes to 3 hours, more preferably 0 to 25° C. for 30 minutes to 1 hour.

Compounds of formula (XI) obtained as above are ligands of the human PPAR protein, PPARδ.

EXAMPLES

The present invention will next be described in detail by way of examples, which should not be construed as limiting the invention.

Example 1

Preparation of methyl 4-methyl-2-[4-(trifluoromethyl)phenyl]thiazole-5-carboxylate [Step A]

4-(Trifluoromethyl)thiobenzamide (20.5 g, 0.1 mol) was dissolved in tetrahydrofuran (300 ml) at room temperature, and then methyl 2-chloroacetoacetate (12.2 ml, 0.1 mol) was added slowly for about 20 minutes therein while stirring. After completion of addition, the mixture was stirred again at room temperature for 30 minutes, and then the mixture was heated and refluxed at 78 to 80° C. for 12 hours. After completion of the reaction, the reaction mixture was cooled to room temperature. Subsequently, 50% aqueous solution of sodium hydroxide (150 ml) was added and stirred for 20 minutes. The resultant organic layer was separated by extraction with ethyl acetate, and dried over magnesium sulfate. The solvent was evaporated under reduced pressure to thereby yield 28.8 g of the title compound (yield: 95.6%).

$^1$H-NMR (300 MHz, CDCl$_3$): 8.01 (d, 2H, J=8.4 Hz), 7.64 (d, 2H, J=8.3 Hz), 3.84 (s, 3H) 2.73 (s, 3H).

Example 2

Preparation of [4-methyl-2-(4-trifluoromethyl-phenyl)thiazole-5-yl]-methanol [Step B]

Methyl 4-methyl-2-[4-(trifluoromethyl)phenyl]]thiazole-5-carboxylate (20.0 g, 66.4 mmol) obtained from Example 1 was dissolved in anhydrous dichloromethane (500 ml) under nitrogen atmosphere, and the reaction mixture was cooled to −78° C. Diisobutyl aluminum hydride (DIBAL-H, 166 ml, 1.0 M hexane solution, 2.5 eq.) was slowly added to the solution for 30 minutes, and the mixture was reacted for another 30 minutes at the same temperature. Subsequently, the temperature was raised to −10° C. and reacted for 30 minutes. After completion of the reaction, an excessive diisobutyl aluminum hydride was removed by ethyl acetate. The resultant residue was extracted by 10% sulfuric acid and ethyl acetate, followed by drying over magnesium sulfate. The resultant mixture was purified on silica flash column, followed by evaporation under reduced pressure to thereby yield 17.5 g of the title compound (yield: 96.4%).

$^1$H-NMR (300 MHz, CDCl$_3$): 7.94 (d, 2H, J=8.1 Hz), 7.63 (d, 2H, J=8.2 Hz), 4.80 (s, 2H), 2.93 (bs, 1H), 2.41 (s, 3H).

$^{13}$C-NMR (78.5 MHz, CDCl$_3$): 164.6, 151.0, 137.0, 133.1, 132.0 (q), 126.8, 126.3 (m), 122.5, 57.1, 15.4.

Example 3

Preparation of 5-bromomethyl-4-methyl-2-[(4-trifluoromethyl)phenyl]thiazole [Step C]

[4-Methyl-2-(4-trifluoromethyl-phenyl)thiazole-5-yl] methanol (15.0 g, 55.0 mmol) obtained from Example 2 was dissolved in anhydrous dichloromethane (300 ml), and then triphenylphosphine (TPP, 5.7 g, 60.0 mmol, 1.1 eq.) and tetrabromomethane (20.0 g, 60.0 mmol, 1.1 eq.) were added to the mixture sequentially at room temperature. After 1 hour, the solvent was evaporated from the reaction mixture under reduced pressure. Subsequently, the remained triphenylphosphine oxide was precipitated by a mixed solvent of hexane and ethyl acetate (v/v=5/1), followed by filtration and evaporation under reduced pressure to thereby yield 17.2 g of the title compound (yield: 93%).

$^1$H-NMR (300 MHz, CDCl$_3$): 8.00 (d, 2H, J=8.1 Hz), 7.67 (d, 2H, J=8.2 Hz), 4.72 (s, 2H), 2.47 (s, 3H).

$^{13}$C-NMR (78.5 MHz, CDCl$_3$): 165.0, 153.8, 136.9, 132.4, 129.7 (q), 127.0, 126.3 (m), 122.5, 23.8, 15.5.

Example 4

Preparation of 5-bromomethyl-4-methyl-2-[(4-trifluoromethyl)phenyl]thiazole [Step C]

[4-methyl-2-(4-trifluoromethyl-phenyl)thiazole-5-yl] methanol (10.0 g, 36.6 mmol) obtained from Example 2 was dissolved in anhydrous dichloromethane 300 ml, and then triphenylphosphine (TPP, 10.6 g, 40.3 mmol, 1.1 eq.) and N-bromosuccinimide (7.17 g, 40.3 mmol, 1.1 eq.) were added to the mixture at room temperature. After 1 hour, the solvent was evaporated from the reaction mixture under reduced pressure. Subsequently, the remained triphenylphosphine oxide was precipitated by a mixed solvent of hexane and ethyl acetate (v/v=5/1), followed by filtration and evaporation under reduced pressure to thereby yield 11.1 g of the title compound (yield: 90.5%).

Example 5

Preparation of 5-chloromethyl-4-methyl-2-[(4-trifluoromethyl)phenyl]thiazole [Step C]

[4-Methyl-2-(4-trifluoromethyl-phenyl)thiazole-5-yl] methanol (5.0 g, 18.3 mmol) obtained from Example 2 was dissolved in tetrachloromethane (300 ml), and then triphenylphosphine (TPP, 6.3 g, 23.8 mmol, 1.3 eq.) was added and the mixture was stirred under reflux for 10 hours. After completion of the reaction, the temperature of the reactor was cooled to room temperature, and a mixed solvent of hexane and ethyl acetate (v/v=5/1) was added thereto to precipitate the remained triphenylphosphine oxide, followed by filtration and evaporation under reduced pressure to thereby yield 8.4 g of the title compound (yield: 78.4%).

$^1$H-NMR (300 MHz, CDCl$_3$): 8.01 (d, 2H, J=8.1 Hz), 7.68 (d, 2H, J=8.2 Hz), 4.79 (s, 2H), 2.51 (s, 3H).

Example 6

Preparation of 5-chloromethyl-4-methyl-2-[(4-trifluoromethyl)phenyl]thiazole [Step C]

[4-Methyl-2-(4-trifluoromethyl-phenyl)thiazole-5-yl] methanol (10.0 g, 36.6 mmol) obtained from Example 2 was dissolved in anhydrous dichloromethane (250 ml) and then triphenylphosphine (TPP, 11.5 g, 44.0 mmol, 1.2 eq.) and N-chlorosuccinimide (5.86 g, 44.0 mmol, 1.2 eq.) were added to the mixture at room temperature. After completion of the reaction, the solvent was evaporated under reduced pressure. Subsequently, the remained triphenylphosphine oxide was precipitated by adding a mixed solvent of hexane and ethyl acetate (v/v=5/1), followed by filtration and evaporation under reduced pressure to thereby yield 10.5 g of the title compound (yield: 98.5%).

Example 7

Preparation of 4-iodo-2-methyl-phenoxy-tert-butyldimethyl silane [Step D]

4-Iodo-2-methylphenol (15.0 g, 64.1 mmol) was dissolved in N,N-dimethylformamide (250 ml), and imidazole (8.7 g, 128.2 mmol, 2.0 eq.) added to the mixture, tert-Butyldimethyl silyl chloride (10.6 g, 70.5 mmol, 1.1 eq.) was slowly added to the above mixture and stirred at room temperature for 4 hours. After completion of the reaction, the reaction mixture was extracted with aqueous ammonium chloride solution and ethyl acetate, and dried over magnesium sulfate. The crude product was purified on silica flash column. The solvent was evaporated under reduced pressure to thereby yield 21.8 g of the title compound (yield: 97.5%).

$^1$H-NMR (300 MHz, CDCl$_3$): 7.47 (d, 1H, J=0.6 Hz), 7.35 (dd, 1H, J=8.4, 2.3 Hz), 6.54 (d, 1H, J=8.4 Hz), 2.18 (s, 3H), 1.03 (s, 9H), 0.22 (s, 6H).

$^{13}$C-NMR (78.5 MHz, CDCl$_3$): 154.3, 139.9, 135.9, 132.3, 121.1, 83.9, 26.2, 18.7, 17.0, −3.8.

Example 8

Preparation of ethyl 4-iodo-2-methyl-phenoxyacetate [Step D]

4-Iodo-2-methylphenol (3.0 g, 12.9 mmol) was dissolved in acetone (250 ml) at room temperature, and then potassium carbonate (2.67 g, 19.4 mmol, 1.5 eq.) was added thereto and vigorously stirred. Ethyl bromoacetate (1.56 ml, 14.1 mmol, 1.5 eq.) was quickly added to the mixture, and then reacted further at room temperature for 4 hours. After completion of the reaction, the reaction mixture was extracted with aqueous ammonium chloride solution and ethyl acetate, and dried over magnesium sulfate. The crude product was purified on silica flash column. The solvent was evaporated under reduced pressure to thereby yield 4.26 g of the title compound (yield: 98.5%).

$^1$H-NMR (300 MHz, CDCl$_3$): 7.45 (d, 1H, J=0.6 Hz), 7.39 (dd, 1H, J=8.5, 2.1 Hz), 6.46 (d, 1H, J=8.5 Hz), 2.18 (s, 3H), 4.59 (s, 2H), 4.24 (q, 2H, J=14.3, 7.1 Hz), 2.24 (s, 3H), 1.28 (t, 3H, J=7.1 Hz).

$^{13}$C-NMR (78.5 MHz, CDCl$_3$): 168.9, 156.3, 139.7, 135.7, 130.4, 113.6, 84.2, 65.9, 61.1, 16.2, 14.4.

Example 9

Preparation of 4-bromo-phenoxy-tert-butyldimethyl silane [Step D]

4-Bromophenol (5.0 g, 29.0 mmol) was dissolved in N,N-dimethylformamide (150 ml), and imidazole (4.09 g, 60.0 mmol, 2.0 eq.) was added to the mixture, tert-Butyldimethyl silyl chloride (4.36 g, 29.0 mmol, 1.0 eq.) was slowly added to the above mixture and stirred at room temperature for 4 hours. After completion of the reaction, the reaction mixture was extracted with aqueous ammonium chloride solution and ethyl acetate, and dried over magnesium sulfate. The crude product was purified on silica flash column. The solvent was evaporated under reduced pressure to thereby yield 8.15 g of the title compound (yield: 97.8%).

$^1$H-NMR (300 MHz, CDCl$_3$): 7.32 (d, 2H, J=8.8 Hz), 6.72 (d, 2H, J=10.0 Hz), 0.98 (s, 9H), 0.18 (s, 6H).

$^{13}$C-NMR (78.5 MHz, CDCl$_3$): 155.3, 132.7, 122.3, 114.0, 26.0, 18.6, −4.1.

Example 10

Preparation of 5-[4-(tert-butyldimethylsilanyloxy)-3-methyl-phenylsulfanyl -methyl]-4-methyl-2-[(4-trifluoromethyl)phenyl]thiazole [Step E]

4-Iodo-2-methyl-phenoxy-tert-butyldimethyl silane (5.0 g, 14.4 mmol) obtained from Example 7 was dissolved in anhydrous tetrahydrofuran (200 ml) under nitrogen atmosphere and cooled to −78° C. tert-Butyllithium (8.47 ml, 1.7 M hexane solution, 1.0 eq.) was slowly added thereto for 1 minute. The mixture was stirred for 10 minutes, and sulfur powder (460 mg, 14.4 mmol, 1.0 eq.) was poured into the mixture at once at the same temperature. The mixture was stirred for 10 minutes to dissolve the said sulfur completely, and 5-bromomethyl-4-methyl-2-[(4-trifluoro -methyl)phenyl]thiazole (4.84 g, 14.4 mmol, 1.0 eq.) obtained from Example 4 was added at once. The reaction temperature was raised to room temperature slowly for about 1 hour to react, followed by terminating the reaction by aqueous ammonium chloride solution. The reaction mixture was extracted with ethyl acetate and brine. Subsequently, the organic layer was dried over magnesium sulfate and the solvent was evaporated by under reduced pressure. The residue was purified by silica gel column chromatography (hexane:ethyl acetate=10: 1) to thereby yield 5.11 g of the title compound (yield: 69%).

$^1$H-NMR (300 MHz, CDCl$_3$): 7.97 (d, 2H, J=8.0 Hz), 7.65 (d, 2H, J=8.2 Hz), 7.17 (4, 1H, J=1.8 Hz), 7.07 (dd, 1H, J=8.2, 2.3 Hz), 6.67 (d, 1H, J=8.3 Hz), 4.10 (s, 2H), 2.20 (s, 3H), 2.15 (s, 3H), 1.00 (s, 9H), 0.20 (s, 6H).

$^{13}$C-NMR (78.5 MHz, CDCl$_3$): 163.4, 154.9, 151.8, 136.8, 132.6, 130.4, 129.6 (q), 126.8, 126.2 (m), 125.2, 119.6, 33.0, 26.1, 18.7, 17.1, 15.2, −3.9.

Example 11

Preparation of 5-[4-(tert-butyldimethylsilanyloxy)-3-methyl-phenylsulfanyl -methyl]-4-methyl-2-[(4-trifluoromethyl)phenyl]thiazole [Step E]

4-Iodo-2-methyl-phenoxy-tert-butyldimethyl silane (5.0 g, 14.4 mmol) obtained from Example 7 was dissolved, while stirring, in anhydrous tetrahydrofuran (150 ml) and diethyl ether 150 ml) under nitrogen atmosphere, and was cooled to −78° C. n-Butyl lithium (9.0 ml, 1.6 M hexane solution, 1.0 eq.) was added thereto for 1 minute. The mixture was stirred for 10 minutes and sulfur powder (460 mg, 14.4 mmol, 1.0 eq.) was poured into the mixture at once at the same temperature. The mixture was stirred for 10 minutes to dissolve the said sulfur completely and 5-chloromethyl-4-methyl-2-[(4-trifluoromethyl)phenyl]thiazole (4.14 g, 14.4 mmol, 1.0 eq.) obtained from Example 5 was added at once. The reaction temperature was raised to room temperature slowly for about 1 hour to react, followed by terminating the reaction by aqueous ammonium chloride solution. The reaction mixture was extracted with ethyl acetate and brine. Subsequently, the organic layer was dried over magnesium sulfate and the solvent was evaporated by under reduced pressure. The residue was purified by silica gel column chromatography (hexane:ethyl acetate=10:1) to thereby yield 5.51 g of the title compound (yield: 78.1%).

Example 12

Preparation of 5-[4-(tert-butyldimethylsilanyloxy)-phenylsulfanylmethyl]-4-methyl-2-[(4-trifluoromethyl)phenyl]thiazole [Step E]

4-Bromo-phenoxy-tert-butyldimethyl silane (5.0 g, 17.4 mmol) obtained from Example 9 was dissolved in anhydrous tetrahydrofuran (300 ml) under nitrogen atmosphere and cooled to −78° C. n-Butyl lithium (10.9 ml, 1.6 M hexane solution, 1.0 eq.) was added thereto for 1 minute. The mixture was stirred for 10 minutes and sulfur powder (557 mg, 17.4 mmol, 1.0 eq.) was poured into the mixture at once at the same temperature. The mixture was stirred for 10 minutes to dissolve the said sulfur completely and 5-chloromethyl-4-methyl-2-[(4-trifluoromethyl)phenyl]thiazole (5.08 g, 17.4 mmol, 1.0 eq.) obtained from Example 5 was added at once. The reaction temperature was raised to room temperature slowly for about 1 hour to react, followed by terminating the reaction by aqueous ammonium chloride solution. The reaction mixture was extracted with ethyl acetate and brine. Subsequently, the organic layer was dried over magnesium sulfate, and the solvent was evaporated by under reduced pressure. The residue was purified by silica gel column chromatography (hexane:ethyl acetate=10:1) to thereby yield 7.3 g of the title compound (yield: 84.6%).

$^1$H-NMR (300 MHz, CDCl$_3$): 7.97 (d, 2H, J=8.0 Hz), 7.65 (d, 2H, J=8.2 Hz), 7.24 (d, 2H, J=8.7 Hz), 7.07 (d, 2H, J=10.0 Hz), 4.08 (s, 2H), 2.20 (s,3H), 2.17 (s, 3H), 0.97 (s, 9H), 0.17 (s, 6H).

Example 13

Preparation of 2-methyl-4-{4-methyl-2-[(4-trifluoromethyl)phenyl]-thiazole -5-yl methylsulfanyl}phenol [Step F]

5-[4-(tert-Butyldimethylsilanyloxy)-3-methyl-phenylsulfanylmethyl]-4-methyl-2-[(4-trifluoromethyl)phenyl]thiazole (5.0 g, 9.8 mmol) obtained from Example 10 was dissolved in tetrahydrofuran (250 ml). Tetrabutylammonium fluoride (TBAF, 24.5 ml, 1 M tetrahydrofuran solution, 2.5 eq.) was slowly added at room temperature. After reaction for 30 minutes, the mixture was extracted with aqueous ammonium chloride solution and ethyl acetate, and the organic layer was dried over magnesium sulfate. The solvent was evaporated under reduced pressure and the residue was purified by silica gel column chromatography (hexane:ethyl acetate 5:1) to thereby yield 3.67 g of the title compound (yield: 94.6%).

$^1$H-NMR (300 MHz, CDCl$_3$): 7.96 (d, 2H, J=8.2 Hz), 7.64 (d, 2H, J=8.3, Hz), 7.20 (d, 1H, J=1.8 Hz), 6.97 (dd, 1H, J=8.2, 2.2 Hz), 6.59 (d, 1H, J=8.2 Hz), 4.06 (s, 2H), 2.19 (s, 3H), 2.09 (s, 3H).

$^{13}$C-NMR (78.5 MHz, CDCl$_3$): 163.9, 155.5, 151.7, 137.4, 133.5, 132.0, 131.7, 131.6, 126.8, 126.3 (m), 125.8, 123.8, 115.7, 33.2, 16.2, 14.8.

Example 14

Preparation of ethyl {2-methyl-4-[4-methyl-2-(4-trifluoromethyl-phenyl)-thiazole-5-yl sulfanyl]phenoxy}acetate [Step G]

2-Methyl-4-{4-methyl-2-[(4-trifluoromethyl)phenyl]-thiazole-5-yl methyl -sulfanyl}phenol (5.0 g, 12.5 mmol) obtained from Example 13 was dissolved in anhydrous tetrahydrofuran (200 ml), and sodium hydride (378 mg, 15.6 mmol, 1.25 eq.) was added at −10° C. Ethyl bromoacetate (2.1 ml, 19.0 mmol, 1.5 eq.) was added for 2 hours while stirring vigorously. After completion of reaction, the mixture was extracted with brine and ethyl acetate, and the organic layer was dried over magnesium sulfate. The solvent was evaporated under reduced pressure, and the residue was purified on silica flash column to thereby yield 4.6 g of the title compound (yield: 76.8%).

$^1$H-NMR (300 MHz, CDCl$_3$): 7.97 (d, 2H, J=8.1 Hz), 7.66 (d, 2H, J=8.3 Hz), 7.21 (d, 1H, J=1.7 Hz), 7.12 (dd, 1H, J=8.4, 2.3 Hz), 6.60 (d, 1H, J=8.4 Hz), 4.62 (s, 2H), 4.24 (q, 2H, J=14.3, 7.1 Hz), 2.24 (s, 3H), 2.21 (s, 3H), 1.28 (t, 3H, J=7.1 Hz).

$^{13}$C-NMR (78.5 MHz, CDCl$_3$): 169.1, 156.8, 151.8, 136.5, 132.5, 131.1, 128.8, 126.8, 126.2 (m), 125.7, 112.0, 66.0, 61.8, 32.9, 16.5, 15.2, 14.5.

Example 15

Preparation of ethyl {2-methyl-4-[4-methyl-2-(4-trifluoromethyl-phenyl)-thiazole-5-yl sulfanyl]phenoxy}acetate [Step G]

2-Methyl-4-{4-methyl-2-[(4-trifluoromethyl)phenyl]thiazole-5-yl methyl -sulfanyl}phenol (10.0 g, 25.3 mmol) obtained from Example 13 was dissolved in acetone (350 ml), and potassium carbonate (8.0 g, 58.2 mmol, 2.3 eq.) was added at room temperature. Ethyl bromoacetate (4.2 ml, 38.0 mmol, 1.5 eq.) was added for 4 hours while stirring vigorously. After completion of reaction, the mixture was extracted with brine and ethyl acetate, and the organic layer was dried over magnesium sulfate. The solvent was evaporated under reduced pressure, and the residue was purified on silica flash column to thereby yield 11.8 g of the title compound (yield: 98.5%).

Example 16

Preparation of 2-{2-methyl-4-[({4-methyl-2-[4-(trifluoromethyl)phenyl]-1,3-thiazole-5-yl}methyl)sulfanyl]phenoxy}acetic acid [Step H]

Ethyl {2-methyl-4-[4-methyl-2-(4-trifluoromethyl-phenyl)thiazole-5-yl sulfanyl]phenoxy}acetate (5.0 g, 10.4 mmol) obtained from Example 15 was dissolved thoroughly in ethanol (300 ml), and 3 N sodium hydroxide solution (35 m) was added. After stirring at room temperature for 30 minutes to complete the reaction, the mixture was adjusted to pH 2.0 with 1 N HCl. The mixture (ca. 80% of ethanol) was evaporated under reduced pressure, and the mixture was extracted with brine and ethyl acetate. The solvent was evaporated under reduced pressure. The residue was dissolved in methanol again and purified by LH-20 column chromatography to thereby yield 4.71 g of the title compound (yield: 98.8%).

$^1$H-NMR (600 MHz, CD$_3$OD): 7.99 (d, 2H, J=8.1 Hz), 7.72 (d, 2H, J=8.3 Hz), 7.17 (s, 1H), 7.14 (dd, 1H, J=8.4, 2.2 Hz), 6.72 (d, 1H, J=8.4 Hz), 4.65 (s, 2H), 4.16 (s, 2H), 2.18 (s, 3H), 2.11 (s, 3H).

$^{13}$C-NMR (150.9 MHz, CD$_3$OD): 172.7, 164.8, 158.2, 152.6, 138.2, 137.5, 133.8, 133.3, 132.5 (q), 129.4, 127.8, 127.2 (m), 126.2, 112.9, 66.3, 32.9, 16.4, 14.8.

INDUSTRIAL APPLICABILITY

As described above, compounds of formula (XI) can be prepared in a high yield easily, according to the present invention.

The invention claimed is:

1. A process for preparing a compound of formula (XI):

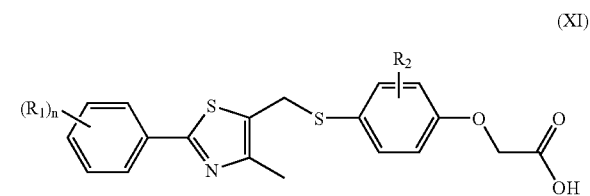

(XI)

wherein R$_1$ represents a hydrogen atom, —CF$_3$, or halogen atom; n is an integer from 0 to 5; and R$^2$ represents a hydrogen atom, a fluorine atom, a chlorine atom, —(C$_1$-C$_4$) alkyl, —O(C$_1$-C$_4$)alkyl, —S(C$_1$-C$_4$)alkyl, or —N(C$_1$-C$_4$alkyl)$_2$ group; wherein the process comprises:

(a) reacting a compound of formula (V):

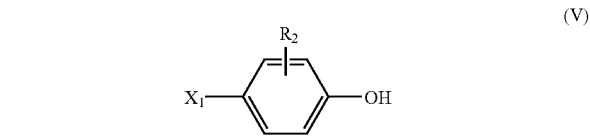

(V)

wherein X$_1$ represents a halogen atom and R$_2$ is as defined in the above, with a phenol-group protecting compound in the presence of a base in a solvent at a temperature from −10° C. to 80° C. for a time from 1 hour to 24 hours to form a compound of formula (VI):

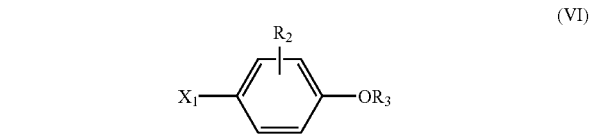

(VI)

wherein X$_1$ and R$_2$ are as defined in the above, and R$_3$ represents a phenol-protecting group having a tetrahydropyranyl, —(C$_1$-C$_4$)alkyl, allyl, or silyl group;

(b) subjecting the compound of formula (VI) to halogen-metal substitution and then introducing sulfur thereto to form a compound of formula (VII):

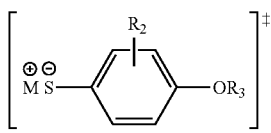

(VII)

wherein $R_2$ and $R_3$ are as defined in the above, and M represents a lithium ion or magnesium halide;

(c) reacting the compound of formula (VII), without separation, with a compound of formula (IV):

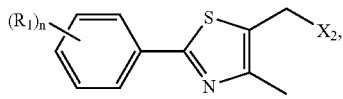

(IV)

wherein $R_1$ and n are as defined in the above, and $X_2$ represents a halogen atom or leaving group which can be displaced by nucleophiles, in an anhydrous solvent at a temperature from −100° C. to 25° C. for a time from 0.5 hour to 24 hours, to form a compound of formula (VIII):

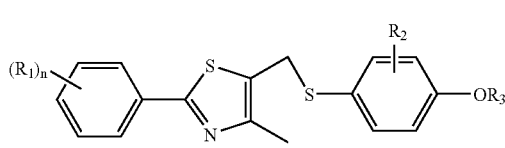

(VIII)

wherein $R_1$, $R_2$, $R_3$ and n are as defined in the above;

(d) eliminating the phenol-protecting group of the compound of formula (VIII) in a solvent at from 0 to 120° C. for from 0.5 hour to 24 hours to form a compound of formula (IX):

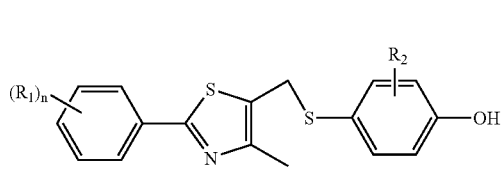

(IX)

wherein $R_1$, $R_2$, and n are as defined in the above;

(e) reacting the compound of formula (IX) with alkyl halogen acetate in the presence of a base in a solvent at a temperature from −10° C. to 120° C. for a time from 0.5 hour to 24 hours to form a compound of formula (X):

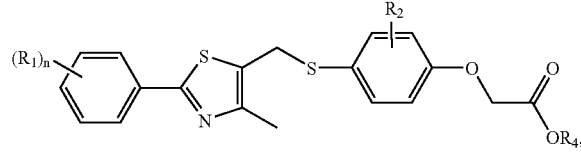

(X)

wherein $R_1$, $R_2$, and n are as defined in the above, and $R_4$ represents a —($C_1$-$C_4$)alkyl group; and (f) hydrolyzing a carboxylic ester of the compound of formula (X) in the presence of a water-soluble inorganic base in an alcohol solvent to form the compound of formula (XI).

2. A process for preparing a compound of formula (XI):

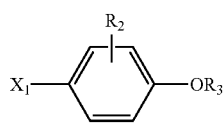

(XI)

wherein $R_1$ represents a hydrogen atom, —$CF_3$, or halogen atom; n is an integer from 0 to 5; and $R_2$ represents a hydrogen atom, a fluorine atom, a chlorine atom, —($C_1$-$C_4$) alkyl, —O($C_1$-$C_4$)alkyl, —S($C_1$-$C_4$alkyl, or —N($C_1$-$C_4$alkyl$)_2$ group; wherein the process comprises:

(a) subjecting a compound of formula (VI):

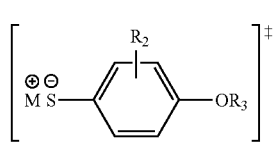

(VI)

wherein $X_1$ and $R_2$ are as defined in the above, and $R_3$ represents a phenol-protecting group having a tetrahydropyranyl, —($C_1$-$C_4$)alkyl, allyl, or silyl group, to halogen-metal substitution and then introducing sulfur thereto to form a compound of formula (VII):

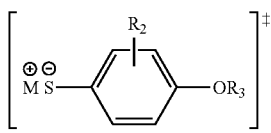

(VII)

wherein $R_2$ and $R_3$ are as defined in the above, and M represents a lithium ion or magnesium halide;

(b) reacting the compound of formula (VII), without separation, with a compound of formula (IV):

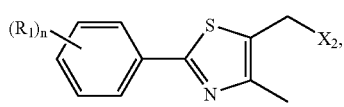

(IV)

wherein $R_1$ and n are as defined in the above, and $X_2$ represents a halogen atom or leaving group which can be displaced by nucleophiles, in an anhydrous solvent at a temperature from −100° C. to 25° C. for a time from 0.5 hour to 24 hours, to form a compound of formula (VIII):

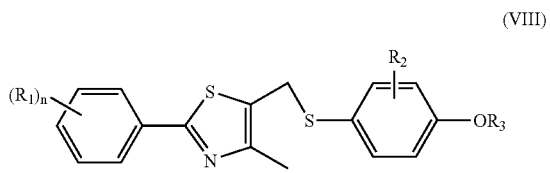
(VIII)

wherein $R_1$, $R_2$, $R_3$ and n are as defined in the above;

(c) eliminating the phenol-protecting group of the compound of formula (VIII) in a solvent at from 0 to 120° C. for from 0.5 hour to 24 hours to form a compound of formula (IX):

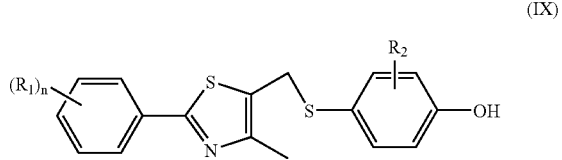
(IX)

wherein $R_1$, $R_2$, and n are as defined in the above;

(d) reacting the compound of formula (IX) with alkyl halogen acetate in the presence of a base in a solvent at a temperature from −10° C. to 120° C. for a time from 0.5 hour to 24 hours to form a compound of formula (X):

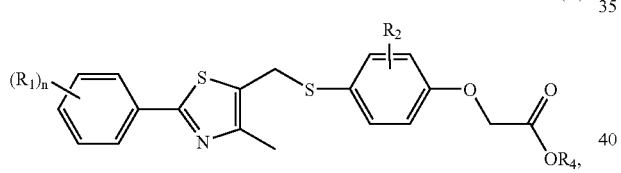
(X)

wherein $R_1$, $R_2$, and n are as defined in the above, and $R_4$ represents a —($C_1$-$C_4$)alkyl group; and (e) hydrolyzing a carboxylic ester of the compound of formula (X) in the presence of a water-soluble inorganic base in an alcohol solvent to form the compound of formula (XI).

3. A process for preparing a compound of formula (XI):

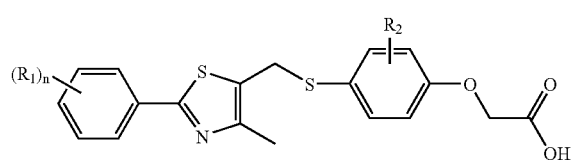
(XI)

wherein $R_1$ represents a hydrogen atom, —$CF_3$, or halogen atom; n is an integer from 0 to 5; and $R_2$ represents a hydrogen atom, a fluorine atom, a chlorine atom, —($C_1$-$C_4$)alkyl, —O($C_1$-$C_4$)alkyl, —S($C_1$-$C_4$)alkyl, or —N($C_1$-$C_4$alkyl)$_2$ group; wherein the process comprises:

(a) reacting a compound of formula (VII)

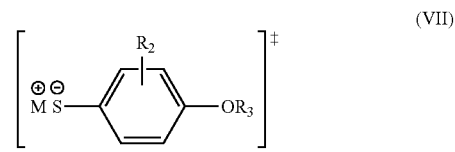
(VII)

wherein $R_2$ is as defined in the above, $R_3$ represents a phenol-protecting group having a tetrahydropyranyl, —($C_1$-$C_4$)alkyl, allyl, or silyl group, and M represents a lithium ion or magnesium halide, with a compound of formula (IV):

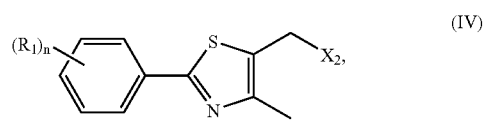
(IV)

wherein $R_1$ and n are as defined in the above, and $X_2$ represents a halogen atom or leaving group which can be displaced by nucleophiles, in an anhydrous solvent at a temperature from −100° C. to 25° C. for a time from 0.5 hour to 24 hours, to form a compound of formula (VIII):

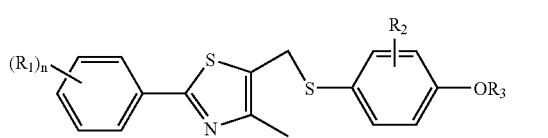
(VIII)

wherein $R_1$, $R_2$, $R_3$ and n are as defined in the above;

(b) eliminating the phenol-protecting group of the compound of formula (VIII) in a solvent at from 0 to 120° C. for from 0.5 hour to 24 hours to form a compound of formula (IX):

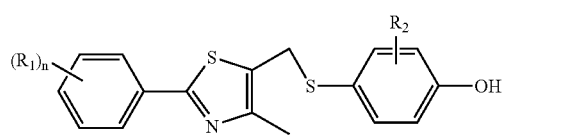
(IX)

wherein $R_1$, $R_2$, and n are as defined in the above;

(c) reacting the compound of formula (IX) with alkyl halogen acetate in the presence of a base in a solvent at a temperature from −10° C. to 120° C. for a time from 0.5 hour to 24 hours to form a compound of formula (X):

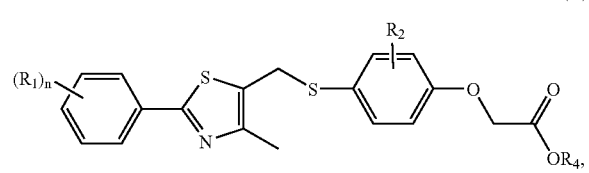
(X)

wherein $R_1$, $R_2$, and n are as defined in the above, and $R_4$ represents a —$(C_1$-$C_4)$alkyl group; and (d) hydrolyzing a carboxylic ester of the compound of formula (X) in the presence of a water-soluble inorganic base in an alcohol solvent to form the compound of formula (XI).

4. The process according to claim 1, wherein $R_3$ represents a phenol-protecting group having an alkylsilyl or alkylarylsilyl group.

5. The process according to claim 1, wherein M represents magnesium chloride, magnesium bromide, or magnesium iodide.

6. The process according to claim 2, wherein $R_3$ represents a phenol-protecting group having an alkylsilyl or alkylarylsilyl group.

7. The process according to claim 2, wherein M represents magnesium chloride, magnesium bromide, or magnesium iodide.

8. The process according to claim 3, wherein $R_3$ represents a phenol-protecting group having an alkylsilyl or alkylarylsilyl group.

9. The process according to claim 3, wherein M represents magnesium chloride, magnesium bromide, or magnesium iodide.

* * * * *